(12) United States Patent
Shao (10) Patent No.: US 6,861,231 B2
(45) Date of Patent: Mar. 1, 2005

(54) SUPPRESSION OF CROSS-REACTIVITY AND NON-SPECIFIC BINDING BY ANTIBODIES USING PROTEIN A

(75) Inventor: Weiping Shao, Cheshire, CT (US)

(73) Assignee: QIAGEN GmbH, Hilden (DE)

( * ) Notice: Subject to any disclaimer, the term of this patent is extended or adjusted under 35 U.S.C. 154(b) by 168 days.

(21) Appl. No.: 09/931,736

(22) Filed: Aug. 17, 2001

(65) Prior Publication Data

US 2003/0036182 A1 Feb. 20, 2003

(51) Int. Cl.$^7$ .............................................. G01N 33/542
(52) U.S. Cl. ................................ 435/7.9; 435/5; 435/6; 435/7.1; 435/7.2; 435/7.92; 435/68.1; 435/69.1; 435/69.7; 435/328; 435/252.33; 530/350
(58) Field of Search ...................... 530/350; 435/252.33, 435/69.7, 69.1, 68, 6, 7.1, 7.2, 5, 7.92, 328

(56) References Cited

U.S. PATENT DOCUMENTS

| | | | | |
|---|---|---|---|---|
| 4,816,567 A | * | 3/1989 | Cabilly et al. | .............. 530/387 |
| 5,476,786 A | * | 12/1995 | Huston | .................. 435/252.33 |
| 5,561,045 A | * | 10/1996 | Dorval et al. | .................. 435/5 |
| 5,665,539 A | | 9/1997 | Sano et al. | |
| 6,087,476 A | * | 7/2000 | Kenten et al. | .............. 530/350 |

* cited by examiner

*Primary Examiner*—James Housel
*Assistant Examiner*—Deborah A. Davis
(74) *Attorney, Agent, or Firm*—Elliot M. Olstein; Alan J. Grant (57) ABSTRACT

The structure, formation and use of blocked antibodies, especially those blocked with Protein A, or active fragments of Protein A, are disclosed as well as processes of producing such antibodies. The uses of such blocked antibodies to achieve significant reduction in both specific cross-reaction and non-specific interaction thereby increasing specificity and reactivity with targeted antigenic sites is also described.

15 Claims, 1 Drawing Sheet

Figure 1

SUPPRESSION OF CROSS-REACTIVITY AND NON-SPECIFIC BINDING BY ANTIBODIES USING PROTEIN A

FIELD OF THE INVENTION

The present invention relates to the field of antibody-antigen interactions and the use of blocked antibodies to effect significant reduction in both specific cross-reaction and non-specific interaction thereby increasing specificity and reactivity with targeted antigenic sites.

BACKGROUND OF THE INVENTION

Antibodies have found great use in the area of diagnostics and for assaying for the presence of antigenic materials in samples such as those derived from biological fluids and for research purposes. A drawback to such successes, however, has been the occurrence of unwanted side reactions in addition to the intended specific reactions of the antibody, which lead to the localization of the antigens under investigation by the specific antibodies used in the assays and the like.

Such unwanted side reactions can include unintended specific reactions, which are frequently considered as cross-reactivity, and which, under certain circumstances, may provide useful information regarding the variations of the structures of the materials under study. Here, the specific binding agent (e.g., the specific antibody used in the assay) recognizes epitopes in molecules other than the antigen under investigation. In addition, there is the often more troublesome unintended non-specific reactions governed by general physico-chemical properties, such as hydrophobic and electrostatic interactions between the antigen and the antibody. Methods to prevent cross-reactivity and non-specific reactions are essential to achieve the lowest background and so to optimize assay performance.

Fragments of immunoglobulins lacking the Fc region (e.g. Fab fragments) have been produced for diagnostic immunoassays for a variety of reasons. The most common reason is to eliminate interference from rheumatoid factor or other heterophilic antibody activity (cross linking), which most often occurs at the Fc region of the antibody. The Fc portion of IgG is also hydrophobic, which has high non-specific binding potential. None of the antigen binding domain of the immunoglobulin resides in the Fc portion; consequently, its removal has little or no effect on antigen binding affinity. One drawback of this approach is that preparation of purified Fab fragments is costly and time-consuming.

Protein A consists of a single polypeptide chain with little or no carbohydrate. The molecule is relatively heat stable and retains its native conformation even after exposure to denaturing reagents. The present invention solves the aforementioned problems by taking advantage of the discovery that Protein A is able to bind specifically to the Fc region of immunoglobulin molecules, which is distant from the antigen binding sites of such immunoglobulins. This invention discloses for the first time an immunoglobulin blocked with Protein A as well as processes using such a blocked structure in the immunological assay of selected analytes. Thus, the present invention relies on using protein A to block the Fc region in such a way as to suppress both cross-reactivity and the non-specific binding associated with this region, and to eliminate the need to generate Fab or other active fragments.

The present invention finds use in immunoassays carried out on microarrays of immobilized antibodies. Measurement of multiple antigens on these microarrays involves use of complex mixtures of antibodies for detection steps in the immunoassay. The use of such mixtures greatly increases the likelihood of non-specific signals, which can significantly reduce the sensitivity and dynamic range of the assay. We have shown that Protein A reduces the non-specific signals associated with the use of complex mixtures of antibodies.

In the past, a number of different molecular weight protein block such as BSA, gelatin, casein, non-fat dry milk, skim milk, normal serum, etc. have been used to prevent non-specific binding.

Protein A not only functions as a normal protein for blocking, but also has a number of advantages over the normal protein block:

1. By specifically binding the Fc portion of antibodies (which causes unintended specific binding) Protein A suppresses cross-reactivity without affecting antigen-antibody binding sites.

2. By specifically binding the Fc portion of antibodies, protein A changes the Fc region's physico-chemical properties (such as hydrophobicity) thereby reducing non-specific binding without affecting antigen-antibody binding sites.

3. With protein A blocking, the Signal/Noise ratio in immunoassays is significantly improved.

BRIEF SUMMARY OF THE INVENTION

In one aspect, the present invention relates to a blocked immunoglobulin comprising an antibody portion and a Protein A portion. In specific embodiments, such blocked immunoglobulin may comprise in its antibody portion one or more light chain variable regions of an antibody with specificity for a given analyte and/or at least one heavy chain variable region of an antibody. In a preferred embodiment, the present invention provides a blocked immunoglobulin wherein the antibody portion comprises two light chain variable regions and two heavy chain variable regions of an antibody. The protein A portion of said blocked immunoglobulins may contain Protein A or an active fragment thereof.

The present invention also relates to such blocked immunoglobulins that are attached to a solid support, such as through a covalent linkage or other chemical adduct or attachment, including via a tether. Such attachment could be through either the antibody portion or the Protein A portion of the blocked immunoglobulin.

In particular embodiments, the solid support is made of a material such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, or polyamino acids, especially glass or plastic.

In other embodiments, the blocked immunoglobulins of the invention are attached to a solid support that further comprises a thin film, membrane, bottles, dishes, fibers, woven fibers, shaped polymers, particles, beads, microparticles, and a combination of the foregoing.

In other embodiments, blocked immunoglobulins of the invention are present in a composition, such as where they are dissolved or suspended in a suitable carrier, including any appropriate diluent or excipient.

The antibody portion of a blocked immunoglobulin of the invention may have structures with different specificities for different analytes. In addition, compositions of the invention may comprise more than one blocked immunoglobulin, some of which may have the same antigenic specificities and some of which may have different antigenic specificities.

The present invention also relates to an array, such as a microarray comprising a solid support attached to a plurality of blocked immunoglobulins of the invention. In some embodiments, the microarray comprises blocked immunoglobulins wherein the antibody portion of each of said blocked immunoglobulins has the same antigenic specificity or has different antigenic specificities, including embodiments wherein the antibody portion of each of said blocked immunoglobulins has a different antigenic specificity. Such microarrays may be present as beads or microparticles and may be composed of porous or non-porous materials.

The present invention also provides for a process for forming a blocked immunoglobulin comprising contacting an antibody with a Protein A compound under conditions promoting the binding of said Protein A compound to said antibody. In preferred embodiments, the protein A compound is protein A or an active fragment thereof. The resulting linkage may be covalent.

In other preferred embodiments of this process, the antibody is attached to a solid support prior to contacting with said Protein A compound. In an especially preferred embodiment of this process, the solid support is chemically quenched prior to attaching the Protein A compound to the antibody.

The present invention also relates to a process for detecting an analyte in a sample comprising contacting an analyte with a blocked immunoglobulin of the invention wherein the antibody portion of said blocked immunoglobulin is specific for said analyte and detecting the binding of said analyte to said blocked immunoglobulin. In a preferred embodiment of such a process, the sample comprises at least two antigenically different analytes. In other preferred embodiments, the analyte is contacted with more than one blocked immunoglobulin, especially where the antibody portion of at least two of said blocked immunoglobulins exhibits a different antigenic specificity.

In an especially preferred embodiment, the sample comprises a plurality of analytes contacted with a plurality of blocked immunoglobulins comprising antibody portions having at least two different antigenic specificities. Such process may take place on a solid support as disclosed herein, including use of a microarray.

In other embodiments of this process, the process may be part of an antibody sandwich assay, an enzyme-linked immunosorbent assay, an antibody dipstick assay, an antibody microarray assay, a radioimmunoassay, or a rolling circle amplification assay or such process may be part of an antibody sandwich assay, an enzyme-linked immunosorbent assay, an antibody dipstick assay, an antibody microarray assay, a radioimmunoassay, or a rolling circle amplification assay. The processes of the invention may also occur on a column, a plate, a microtitre dish, a dipstick, a cell sample or a tissue sample, or in situ.

The present invention also provides a process for detecting an analyte in a sample wherein said analyte comprises a rolling circle replication primer and wherein detection of binding of analyte to blocked immunoglobulin is accomplished by contacting said bound analyte with an amplification target circle (ATC) comprising a primer complementary sequence complementary to a portion of said primer under conditions promoting rolling circle amplification and wherein the production of tandem sequence DNA (TS-DNA) indicates the presence of said analyte. Such process may occur on a microarray.

The present invention also provides a process of detecting an analyte wherein a blocked immunoglobulin comprises a rolling circle replication primer and wherein detection of binding of analyte to blocked immunoglobulin is accomplished by contacting said bound analyte with an amplification target circle (ATC) comprising a primer complementary sequence complementary to a portion of said primer under conditions promoting rolling circle amplification and wherein the production of tandem sequence DNA (TS-DNA) indicates the presence of said analyte. Such process may also be part of a microarray. Such analyte may comprise a protein.

DETAILED DESCRIPTION OF THE INVENTION

The present invention relates to a blocked immunoglobulin comprising an antibody portion and a Protein A portion. In specific embodiments, the antibody portion comprises at least one light chain variable region of an antibody and/or at least one heavy chain variable region of an antibody. Commonly, there will be at least two light chain and two heavy chain regions, which may include both constant and variable regions.

With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all antibodies have a similar overall 3 dimensional structure. This structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, *J. Biol. Chem.* 252:6609–6616 (1977). The numbering scheme is shown in the figures, where the CDRs are underlined and the numbers follow the Kabat scheme.

In all mammalian species, antibody polypeptides contain constant (i.e., highly conserved) and variable regions, and, within the latter, there are the CDRs and the so-called "framework regions" made up of amino acid sequences within the variable region of the heavy or light chain but outside the CDRs.

The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain. Such antibodies may also include fragments, such as Fab and F(ab$_2$)' fragments, capable of reacting with and binding to any of the polypeptides disclosed herein as being receptors.

The blocked immunoglobulin of the invention may also have an antibody portion that comprises at least one antigen-reactive fragment of an antibody. However, while the presence of such a fragment, as disclosed herein, does not in any way limit the invention, it should be understood that a major advantage of the invention is that it obviates the need to form such active fragments in order to avoid the unwanted side reactions produced by the presence of an Fc region. Thus, by using the blocked immunoglobulins of the invention there is little or no need to generate immunologically active fragments of antibodies although these may find use in some instances, such as where a blocked immunoglobulin comprises a whole light and heavy chain as a dimer and the Fc portion of the heavy chain constant region has been blocked with a protein A compound.

As used herein the term "Protein A compound" refers to protein A, a fragment of protein A, or a variant of protein A that can interact with the Fc region of an antibody. This includes recombinant forms of protein A and proteolytic fragmens of protein A (as described, for example, in *J. Chromat.* 597:527–562 (1992)).

In preferred embodiments, the protein A compound is protein A itself. Protein A has two different forms, the native one which is from *Staphylococus aureus,* and the recombinant one which is a genetically truncated version. Both forms of protein A exhibit the same affinity for Ig G molecules, and have been proved effective for blocking cross-reactivity and non-specific binding. Besides microarry-based assay, this invention can also be applied in other solid-phase and antibody based protein assays or immunoassays. In addition to the procedures described herein, the blocking procedures and conditions of protein A with antibodies can be changed or optimized for specific applications. Proteolytic treatment of Protein A to generate univalent fragments (*J. Chromat.* 597, 257–62 (1992)

In accordance with the foregoing, the present invention relates to a blocked immunoglobulin of the invention wherein said Protein A portion comprises at least one protein A compound. In specific embodiments, the Protein A compound is a fragment of Protein A so long as said fragment is able to bind to the Fc region of the antibody portion of the immunoglobulins of the invention.

In a preferred embodiment, the present invention is directed to a blocked immunoglobulin as disclosed herein and further comprising a solid support to which this blocked immunoglobulin is attached. Commonly, but not exclusively, this attachment is through a covalent linkage but other types of bonds are possible so long as they do not defeat the utility of the invention or interfere with the ability of Protein A to bind the antibody portion of the immunoglobulin. Such attachment may optionally include the use of a tether. Such antibody readily serves as the capture antibody in a typical sandwich assay.

Commonly, the blocked immunoglobulins of the invention are attached to the solid support through a linkage of the antibody portion of the blocked immunoglobulin but attachment through the protein A portion is possible so long as this does not compromise the increased specificity of the blocked immunoglobulin. Such attachment may or may not include the use of a tether.

In specific embodiments of the invention, the blocked immunoglobulins disclosed herein are attached to a solid support made of a material including any of the following non-limiting or exhaustive list. Thus, such materials may include acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, polyamino acids, or combinations of these, with glass and plastic being highly preferred.

The solid supports useful in the present invention may be in the form of a thin film, membrane, bottles, dishes, fibers, woven fibers, shaped polymers, particles, beads, microparticles, or any combination of the foregoing.

The present invention also relates to compositions comprising at least one blocked immunoglobulin of the invention in a suitable carrier, which includes all suitable diluents or excipients. The blocked immunoglobulins of the invention may be suspended, dissolved or otherwise contained in such carrier and the specific form of the composition or identity of the carrier is in no way limiting of the invention so long as it in no way detracts from the essential structure and function and other identifying characteristics of the invention.

Of course, such compositions need in no way contain only one blocked immunoglobulin or one kind of blocked immunoglobulin but may contain any number of range of blocked immunoglobulins encompassed by the invention disclosed herein. The blocked immunoglobulins contained in such a composition may be blocked immunoglobulins having the same or different specificities and may include compositions wherein one or more of the blocked immunoglobulin entities in the composition have the same specificity and wherein one or more of the blocked immunoglobulin entities in the composition have different specificities.

As used herein, the term "specificity" means antigenic specificity and serves to denote the immunological characteristics of the antibody portion of the blocked immunoglobulins of the invention. Thus, where the antibody portion of a blocked immunoglobulin of the invention binds more tightly to a particular substrate, or analyte, or antigen, or antigenic determinant, as those terms are used in the art, such as where the latter is a protein or polypeptide, than it does to, say, a protein or polypeptide with different antigenic properties, as where the proteins or polypeptides differ in amino acid sequence so as to produce different antigenic determinants, a different blocked immunoglobulin molecule of the invention that binds preferentially to that same protein or polypeptide is deemed to have the same or similar specificity while a blocked immunoglobulin of the invention that does not bind preferentially to the same polypeptide or protein as another blocked immunoglobulin of the invention is deemed to have a different specificity.

The processes of the present invention greatly facilitate the use of blocked immunoglobulins with multiple analytes in a sample and are particularly useful when presented as part of an array, such as a microarray, using multiple blocked immunoglobulins attached to a surface or other substrate and then contacted with a sample containing one or more analytes to be detected. Thus, the present invention specifically contemplates a microarray comprising a solid support attached to a plurality of blocked immunoglobulins according to the disclosure herein. In a particular embodiment thereof, the microarray of the invention has the antibody portion of each of the blocked immunoglobulins attached directly to the substrate or else attached through a tether, such as a molecule polymer of varying length that effective holds the blocked immunoglobulins to the array.

In one such embodiment, the whole procedure may be part of a sandwich assay, wherein the capture antibody is a blocked immunoglobulin of the invention that reacts with an analyte that is itself then contacted with an additional antibody that may optionally be attached to an oligonucleotide primer for use in rolling circle amplification as a means of detecting the detection and binding of the analyte by the capture antibody.

In specific embodiments of such an array, the blocked immunoglobulins attached thereto may have the same antigenic specificity or may be of differing specificity, just as described for blocked immunoglobulins of the invention that are not so attached to an array or other substrate.

In accordance with the foregoing, the present invention provides methods and compositions for the preparation and use of a substrate having a plurality of structures like the blocked immunoglobulins, acting as probes, in predefined regions of the substrate, such as a solid substrate or solid support. This substrate with attached probes or blocked immunoglobulins, is called a "microarray" or "chip," and is used in screening a variety of structures as ligands for binding with specific probes (i.e., the blocked immunoglobulins of the invention). In forming such an array, it may be necessary to attach said blocked immunoglobulins to the substrate using other linking structures, such as various linking molecules, or "tethers," but in all cases such linkers will in no way detract from the ability of blocked immunoglobulins to bind the analyte to be determined. Methods of forming such arrays are described in the literature (see the list or protein array references below). As used in the present invention, such microarrays will commonly be of the order of about 1 square centimeter. Larger or smaller arrays are technologically possible and may find use where the analytes to be determined are varying in number and can conveniently be determined simultaneously or in sequence.

In accordance with the foregoing, the microarray of the present invention includes blocked immunoglobulins wherein the antibody portion of at least two of the blocked immunoglobulins have different antigenic specificities. This is readily extended to three, four or more using the technology provided herein. Thus, the present invention readily includes embodiments wherein the antibody portion of each of the blocked immunoglobulins has a different antigenic specificity.

The microarrays of the present invention comprise substrates made of acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, or polyamino acids, including combinations of these. Where the substrate is composed of glass, prior chemical modification of the surface may be required but will generally involve only procedures well known in the art for preparing glass surfaces for binding to macromolecules.

In addition, such arrays need not be flat surfaces but may include such structures as beads or microparticles and the surfaces of such microarrays may be porous or otherwise.

The present invention also relates to a process for forming a blocked immunoglobulin comprising contacting an antibody with a Protein A compound under conditions promoting the binding of said Protein A compound to said antibody. In a preferred embodiment, the Protein A compound is Protein A. In other preferred embodiments, the protein A compound is a fragment of Protein A.

In another preferred embodiment, the present invention comprises a process wherein the antibody forms a covalent linkage with the Protein A compound. The process of the invention also includes cases where the antibody is attached to a solid support prior to contacting with said Protein A compound to form the blocked immunoglobulins of the invention. As before, such solid support may be porous and may be in the form of beads or microparticles.

A preferred process for forming the blocked immunoglobulins of the invention is to pre-block antibodies involved in the assays using protein A for the blocking agent. For example, in using solid-phase-based assays, the following procedures could be advantageously included in the assay procedures:
(1) block the solid phase sequentially:
   (a) Quench the activated groups with small molecules such as: Glycine, Lysine or NaBH4 depending on activation chemistry of solid surface.
   (b) Incubate the primary antibodies which are immobilized on the solid phase with 0.5 mg/ml protein A at 37° C. for 30 min.
   (c) Incubate the primary antibodies which are immobilized on the solid phase with normal blocking buffer (50 mM Glycine, pH 9.0, 2 mg/ml BSA, 5% non fat dry milk) containing 0.5 mg/ml protein A at 37° C. for 30 min before reaction with antigen.
(2) Pre-incubate the secondary antibodies with 0.5 mg/ml protein A at 37° C. for 30 min before adding to react with antigen.
(3) Pre-incubate the antibody conjugate which is used for detection with 0.5 mg/ml protein A at 37° C. for 30 min before adding to react with the secondary antibodies.

Procedures 1, or 2, or 3 could each be used in the alternative to provide the appropriate blocking of the immunoglobulin. Here, the secondary antibody might be part of a partial sandwich assay. In one non-limiting example, the capture antibody is a blocked anti-body that binds to an analyte, such as a polypeptide whose presence in a sample is to be detected and/or quantitated. A secondary antibody (which also may be a blocked immunoglobulin within the invention) is then contacted with said analyte bound to the capture antibody to complete the sandwich. This secondary antibody is itself optionally attached to a primer oligonucleotide for use in a rolling circle amplification (RCA) as disclosed herein by contacting said primer with an amplification target circle (ATC) and enzymes that perform rolling circle amplification and under conditions (including the presence of appropriate and optionally labeled deoxynucleoside triphosphates (dNTPs)) promoting said amplification. In another embodiment, the secondary antibody may be attached to a ligand, such as where the second antibody is biotinylated, and reacted with an anti-biotin conjugate, such as a streptavidin and an anti-streptavidin antibody, that is itself attached to an RCA primer for rolling circle amplification. Such antibodies may include anti-mouse antibodies and anti-rabbit antibodies from sera or may be some form of recombinant or monoclonal antibody. In performing such assays, the capture antibody is conveniently attached to some type of solid support, possibly one made of glass or plastic, and which may be in the form of an array, such as a microtitre plate, or beads, microspheres, and the like.

Figure 1:
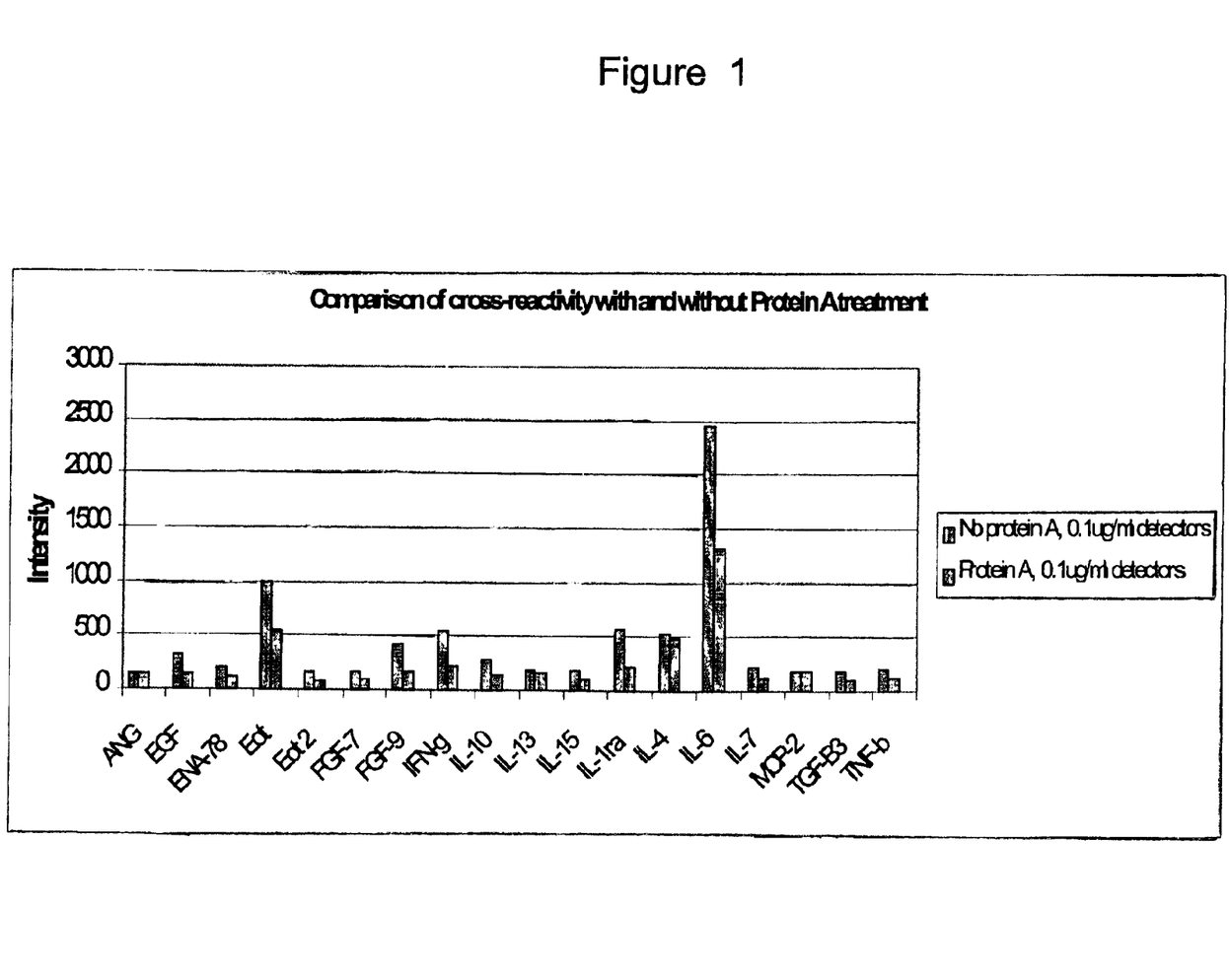
FIG. 1 shows reduction of non-specific signals for a cross-reactivity experiment using Protein A-blocked immunoglobulin versus non-protein-A blocked antibody.

By way of example only, for the results of FIG. 1, the following procedure was used:

Procedure:
1. Block: (1) Glycine, 37° C., 30 min; (2) 0.5 mg/ml protein A, 37° C., 30 min; (3) normal blocking buffer+0.5 mg/ml protein A, 37° C., 30 min.
2. Secondary antibodies: (1) pre-incubate mixture of 20 biotinylated secondary antibodies with 0.5 mg/ml protein A at 37° C., 30 min; (2) incubate at 37° C. for 30 min.
3. Antibody-RCA Conjugate: (1) pre-incubate anti-biotin antibody conjugate with 0.5 mg/ml protein A; (2) pre-anneal with ATC circle; (3) incubate at 37° C. for 30 min.
4. LRCA reaction/decoration: RCA reaction solution containing T7 native DNA polymerase (0.01 units/ul)/1 mM dNTPs/0.03 mg/ml ssDNA-binding protein/1×sequenase/ 8% DMSO/0.05 uM Cy5-labeled DNA decorator, incubate at 37° C. for 30 min. 5. Dry and scan slides for Cy5 fluorescence In accordance with the foregoing, the present invention further relates to a process comprising quenching the solid support prior to contacting the antibody with the Protein A compound. In preferred embodiments of such a process, the antibody and Protein A are contacted at a temperature of at least about 37° C., especially wherein said contacting occurs for at least about 30 minutes.

In other preferred embodiments thereof, following said contacting with Protein A the blocked immunoglobulin is further contacted with a blocking agent other than a Protein A compound. The blocking agent may be other than a Protein A compound, such as bovine serum albumin (BSA). In other preferred embodiments, the Protein A compound is Protein A, especially where said Protein A is present at a concentration of at least about 0.5 mg/ml, most especially where the Protein A is present at a concentration of about 0.5 mg/ml.

The present invention finds wide use in all antibody-based applications such as protein assays in proteomics, immunodiagnostic tests in clinical science, forensic science, and environmental analysis.

In accordance with such uses, the present invention relates to a process for detecting an analyte in a sample comprising contacting an analyte with a blocked immunoglobulin as disclosed herein where the antibody portion of said blocked immunoglobulin is specific for said analyte and detecting the binding of said analyte to said blocked immunoglobulin. In preferred embodiments, the sample comprises at least two antigenically, possibly more, different analytes and the analyte may be contacted with more than one blocked immunoglobulin. Commonly, the antibody portion of at least two, possibly more, of said blocked immunoglobulins exhibits a different antigenic specificity. In a preferred embodiment, the present invention relates to a process as disclosed herein where the sample comprises a plurality of analytes contacted with a plurality of blocked immunoglobulins comprising antibody portions having at least two different antigenic specificities. Such a process is extremely well suited to use of a microarray as disclosed herein.

In such cases, the blocked immunoglobulins of the invention may include multiple structures comprising more than one antibody and more than one protein A compound in the same molecule, which may or may not be attached to a solid support or substrate. In such cases, a blocked immunoglobulin may exhibit multiple antigenic specificities. In other cases, the property of multiple specificities may depend on the presence, in composition or as part of a solid support or substrate, of multiple blocked immunoglobulins each of which has a single antigenic specificity but where the specificity varies from one blocked immunoglobulin to another. Thus, for example, in a given composition, or as part of a given microarray, there may be a plurality of blocked immunoglobulins contained on a single chip or microarray wherein have a given antigenic specificity or differ in that some are specific for a particular type of antigenic structure, such as a given protein or polypeptide while one or more of the other blocked immunoglobulins on the same chip, or in the same composition, or solution, or suspension, are specific for a different antigenic structure, such as a different protein or polypeptide and wherein the differences between the antigenic structure may be slight or great so long as the difference is sufficient to permit the blocked immunoglobulins housed on a given array, or contained in a different composition, to detect the difference in such antigenically active analytes. Thus, any desired combination or permutation of the blocked immunoglobulins of the invention may be used, either attached to a solid support or substrate or not so attached. This can include blocked immunoglobulins in which a given molecule comprises an antibody portion that comprises more than one antibody structure, wherein each of the antibodies in said antibody portion has the same or different antigenic specificity. In the same way, the Protein A portion may include more than one Protein A structure, either Protein A itself or active fragments thereof (meaning fragments capable of blocking the Fc portion of an antibody). For example, two antibodies blocked with two Protein A compounds would form two blocked immunoglobulins but the latter, when linked together, such as by some type of tether or other convenient molecular structure, could then form a single blocked immunoglobulin within the present invention.

Thus, such blocked immunoglobulins may be attached to a solid support, such support being a substrate as described herein for solid supports and thus may be of a porous material or in the form of beads and the like as disclosed elsewhere herein.

By way of non-limiting example, the present invention relates to a process for detecting an analyte in a sample comprising contacting an analyte with a microarray of the invention wherein the antibody portion of at least one of the blocked immunoglobulins on said microarray is specific for said analyte and detecting binding of an analyte to at least one blocked immunoglobulin on said microarray. In one such embodiment, the sample contains a plurality of antigenically different analytes. In another such embodiment, the microarray comprises a plurality of blocked immunoglobulins comprising antibody portions exhibiting a plurality of different antigenic specificities.

In accordance with the present invention, such processes, whether they employ the blocked immunoglobulins of the invention as part of a composition and suspended or dissolved in a suitable carrier or whether the blocked immunoglobulins are attached to a support, such as where they are part of a microarray, may be part of an antibody sandwich assay, an enzyme-linked immunosorbent assay, an antibody dipstick assay, an antibody microarray assay, a radioimmunoassay, or a rolling circle amplification assay.

The processes of the invention for detecting an analyte may occur on a column, a plate, a microtitre dish, a dipstick, a cell sample or a tissue sample, and may even be carried out in situ. For use with a microarray, one preferred type of substrate would be a microtitre plate, such as a 96 well or other size dish.

Among the methods of detecting binding of analyte to a blocked immunoglobulin of the invention are the use of any number of detector molecules, including all types of labels, such as fluorescent and radiolabels. The analyte or one or more of the blocked immunoglobulins may be linked to such a label or may be linked to a structure that itself may be used to detect the binding of the analyte.

In one such embodiment, the analyte and/or the blocked immunoglobulin is linked to an oligonucleotide that can serve as a primer for oligonucleotide amplification, for example, rolling circle amplification (RCA), the characteristics of which are well known in the art.

In accordance therewith, the present invention relates to a process for detecting an analyte wherein said analyte comprises a rolling circle replication primer and wherein detection of binding of analyte to blocked immunoglobulin is accomplished by contacting said bound analyte with an amplification target circle (ATC) comprising a primer complementary sequence complementary to a portion of said primer under conditions promoting rolling circle amplification and wherein the production of tandem sequence DNA (TS-DNA) indicates the presence of said analyte.

Any form of RCA may be used with the processes disclosed herein. For example, linear rolling circle amplification (LRCA) uses a primer annealed to a circular target DNA molecule and DNA polymerase is added. The amplification target circle (ATC) forms a template on which new DNA is made, thereby extending the primer sequence as a continuous sequence of repeated sequences complementary to the circle but generating only about several thousand copies per hour. An improvement on LRCA is the use of exponential RCA (ERCA), with additional primers that anneal to the replicated complementary sequences to provide new centers of amplification, thereby providing exponential kinetics and increased amplification. Exponential rolling circle amplification (ERCA) employs a cascade of strand displacement reactions, also referred to as HRCA (Lizardi, P. M. et al. *Nature Genetics,* 19, 225–231 (1998)). In accordance with the foregoing, any type of rolling circle amplification may be utilized, including procedures involving multiple primers attaching to the same ATC as well as multiple layers and multiple rounds of rolling circle amplification. Such methods of detection include those recited in U.S. patent application Ser. No. 09/506,192, filed Jun. 28, 2000, U.S. patent application Ser. No. 09/577,444, filed May 24, 2000, and U.S. patent application Ser. No. 60/299,345, filed Jun. 19, 2001, the disclosures of which are hereby incorporated by reference in their entirety.

The oligonucleotide primers useful such processes can be of any desired length so long as they can be bound to an analyte or to an analyte or can be bound to an antibody structure or protein A structure as disclosed herein. For example, such primers may be of a length of from at least 2 to about 30 to 50 nucleotides long, preferably about 2 to about 35 nucleotides in length, most preferably about 5 to about 10 nucleotides in length, with hexamers and octamers being specifically preferred embodiments. Such primers as are used herein may equally be specific only, or random only, or a mixture of both, with random primers being especially useful and convenient to form and use.

In RCA, a primer bound to an ATC produces a replication fork as it is extended by the DNA polymerase around the ATC. The larger an ATC is, the more amplification forks that could be formed and thus a given ATC may attract primers bound to different analytes.

The oligonucleotide primers useful in the processes of the present invention will have segments complementary to a portion of the ATC. Amplification target circles (ATCs) useful in the processes of the present invention are circular DNA or RNA molecules, either single or double stranded, including DNA-RNA hybrid molecules generally containing between 40 to 10,000 nucleotides. However, it is expected that there will be no upper limit to the size of the ATC. Where the ATC is a duplex circle, such numbers are intended to refer to base pairs rather than individual nucleotide residues. The ATCs useful in the processes disclosed herein may have functionally different portions, or segments, making them particularly useful for different purposes. At least one such portion will be complementary to an oligonucleotide primers and, when present, is referred to as a primer complementary portion or site.

Amplification target circles (ATCs) useful herein comprise target sequences to be amplified as a means of detecting bound analyte. Previous technologies for RCA are known and these have utilized RCA for such signal detection [see, for example, Lizardi, U.S. Pat. No. 5,854,033, the disclosure of which is hereby incorporated by reference in its entirety]. The amplification target circles utilized as templates for the amplification disclosed for use with the present invention may be either single stranded DNA circles or duplex (double stranded) DNA circles but are commonly single stranded. Where said ATCs are duplex, it may be desirable that at least one strand of said duplex contains a nick. Such nicks are commonly present in duplex circles but they may also be introduced into such circles, such as by enzymatic methods well known in the art, if not already present therein. Where duplex circles are employed, amplification will commonly occur from both strands as templates. Simultaneous amplification of both circles may or may not be desirable.

In some circumstances it may be desirable to quantitatively determine the extent of amplification occurring and/or the amount of TS-DNA being formed or, in some circumstances, to be able to measure in a discriminating fashion the relative quantities of amplification target circles being formed where the ATCs of the starting mixture are not uniform in structure and/or size. In such instances, the present invention works well with any number of standard detection schemes, such as where special deoxynucleoside triphosphates (dNTPs) are utilized that make it easier to do quantitative measurements. The most common example is where such nucleotide substrates are radiolabeled or have attached thereto some other type of label, such as a fluorescent label or the like. Again, the methods that can be employed in such circumstances are many and the techniques involved are standard and well known to those skilled in the art. Thus, such detection labels include any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. General examples include radioactive isotopes, fluorescent molecules, phosphorescent molecules, enzymes, antibodies, and ligands.

In such cases, the dNTPs used to form the TS-DNA products may contain structures capable of binding to detector molecules. For example, said nucleotide units in the TS-DNA may include decorator molecules that can bind to detectors useful in determining the presence and amount of TS-DNA formed from the rolling circle amplification procedure. For example, such structures may bind haptens for which antibodies are specific anf thus labeled antibodies can be used to attach to the haptens thereby quantitating the amount of TS-DNA product produced since this will be proportional to the amount of hapten bound to the TS-DNA. The antibodies used to bind the haptens will themselves be labeled, such as with a fluorescent label or by being biotinylated, although the exact nature of such labeling is in no way limiting of the present invention.

Examples of suitable fluorescent labels include CyDyes such as Cy2, Cy3, Cy3.5, Cy5, And Cy5.5, available from Amersham Pharmacia Biotech (U.S. Pat. No. 5,268,486). Further examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, Oreg. and Research Organics, Cleveland, Ohio.

Labeled nucleotides are a preferred form of detection label since they can be directly incorporated into the products of RCA during synthesis. Examples of detection labels that can be incorporated into amplified DNA include nucleotide analogs such as BrdUrd (Hoy and Schimke, *Mutation Research*, 290:217–230 (1993)), BrUTP (Wansick et al., *J. Cell Biology*, 122:283–293 (1993)) and nucleotides modified with biotin (Langer et al., *Proc. Natl. Acad. Sci. USA*, 78:6633 (1981)) or with suitable haptens such as digoxygenin (Kerkhof, *Anal. Biochem.*, 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label is Biotin-16-uridine-5'-triphosphate (Biotin-16-dUTP, Boehringher Mannheim). Radiolabels are especially useful for the amplification methods disclosed herein. Thus, such dNTPs may incorporate a readily detectable moiety, such as a fluorescent label as described herein.

The present invention provides a means to achieve signal amplification in a variety of methods. In this case, the goal is to amplify a signal that allows detection of the binding or non-binding of an analyte. In methods including, but not limited to cases where a DNA is detected by annealing of a labeled probe or by incorporation of a labeled nucleotide, or by labeling DNA product after synthesis, for example, by covalent modifications or intercalation of detectable molecules, the present invention provides a way to amplify DNA product and thereby signal intensity.

In one such embodiment, an analyte comprising (for example, attached to) an oligonucleotide primer is to be detected, or otherwise determined or quantitatively measured. A sample containing such an analyte is contacted with one or more blocked immunoglobulins of the invention, such as where these are present on an array, and allowed to interact. The array can then be washed to remove unbound analyte (for example, a protein present in the sample) and the array then contacted with a source of amplification target circles and under conditions (enzyme, dNTPs, Mg ions, buffer, etc.) to promote rolling circle amplification which, when it occurs, indicates the presence of oligonucleotide primers (and bound analyte) on the array, thereby indicating the presence of analyte in the sample previously contacted with the array.

In accordance with the foregoing, the present invention also relates to such a process wherein said analyte comprises a rolling circle replication primer and wherein detection of binding of analyte to blocked immunoglobulin is accomplished by contacting said bound analyte with an amplification target circle (ATC) comprising a primer complementary sequence complementary to a portion of said primer under conditions promoting rolling circle amplification and wherein the production of tandem sequence DNA (TS-DNA) indicates the presence of said analyte. Commonly, said analyte will comprise a protein or polypeptide structure.

Alternatively, the present invention also comprises a process wherein the blocked immunoglobulin comprises a rolling circle replication primer and wherein detection of binding of analyte to blocked immunoglobulin is accomplished by contacting said bound analyte with an amplification target circle (ATC) comprising a primer complementary sequence complementary to a portion of said primer under conditions promoting rolling circle amplification and wherein the production of tandem sequence DNA (TS-DNA) indicates the presence of said analyte. In other embodiments, the blocked immunoglobulins are attached to a microarray as described herein.

Thus, the process for analyzing for an analyte according to the invention includes a method comprising the steps of:

(a) mixing or otherwise contacting a blocked antibody composition with a target sample comprising an analyte wherein a rolling circle replication primer is coupled to the blocked antibody composition, wherein the blocked antibody composition binds to the analyte, (b) mixing or otherwise contacting the rolling circle replication primer with an amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, and (c) mixing or otherwise contacting DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

In a preferred embodiment, the present invention includes a process for detecting proteins, the method comprising the steps of:

(a) mixing or otherwise contacting a blocked antibody composition with a target sample comprising a target molecule wherein a rolling circle replication primer is coupled to the blocked antibody composition, wherein the blocked antibody composition binds to the target molecule, wherein the target molecule is a protein, (b) mixing or otherwise contacting the rolling circle replication primer with an amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, and (c) mixing or otherwise contacting DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

In accordance with the foregoing, the present invention relates generally to a process for detecting analytes, the method comprising an amplification operation, wherein an amplification target circle is coupled to a blocked antibody composition, wherein the blocked antibody composition can interact with an analyte, wherein the amplification operation comprises rolling circle replication of the amplification target circle to produce tandem sequence DNA.

In a preferred embodiment of such a process, the present invention contemplates a process for detecting a protein analyte, the method comprising the steps of:

an amplification operation, wherein an amplification target circle is coupled to a blocked antibody composition, wherein the blocked antibody composition can interact with a target molecule, wherein the target molecule is a protein, wherein the amplification operation comprises rolling circle replication of the amplification target circle to produce tandem sequence DNA.

In one such embodiment, the present invention relates generally to a process for detecting analytes, the method comprising the steps of:

(a) mixing or otherwise contacting a blocked antibody composition with a target sample comprising an analyte wherein an amplification target circle is coupled to the blocked antibody composition, wherein the blocked antibody composition binds to the analyte, (b) mixing otherwise contacting a rolling circle replication primer with the amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, and (c) mixing otherwise contacting a DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

In a preferred embodiment, the present invention further relates to a process for detecting proteins, the method comprising the steps of:

(a) mixing or otherwise contacting a blocked antibody or immunoglobulin composition with a target sample comprising a target molecule wherein an amplification target circle is coupled to the blocked antibody composition, wherein the specific binding molecule binds to the target molecule, wherein the target molecule is a protein, (b) mixing or otherwise contacting a rolling circle replication primer with the amplification target circle, to produce a primer-ATC mixture, and incubating the primer-ATC mixture under conditions that promote hybridization between the amplification target circle and the rolling circle replication primer in the primer-ATC mixture, wherein the amplification target circle comprises a single-stranded, circular DNA molecule comprising a primer complement portion, wherein the primer complement portion is complementary to the rolling circle replication primer, and (c) mixing or otherwise contacting DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

The present invention also relates to a process for detecting analytes in a sample, the method comprising the steps of:

a DNA ligation operation and an amplification operation, wherein the DNA ligation operation comprises circularization of an open circle probe, wherein circularization of the open circle probe is dependent on hybridization of the open circle probe to a target sequence, wherein the target sequence is coupled to a blocked antibody composition, wherein the blocked antibody composition can interact with an analyte, wherein the amplification operation comprises rolling circle replication of the circularized open circle probe to produce tandem sequence DNA.

In a preferred embodiment, the present invention further contemplates a process for detecting proteins, the method comprising the steps of:

a DNA ligation operation and an amplification operation, wherein the DNA ligation operation comprises circularization of an open circle probe, wherein circularization of the open circle probe is dependent on hybridization of the open circle probe to a target sequence, wherein the target sequence is coupled to a blocked antibody composition, wherein the specific binding molecule can interact with a target molecule, wherein the target molecule is a protein, wherein the amplification operation comprises rolling circle replication of the circularized open circle probe to produce tandem sequence DNA.

The present invention also relates to a process for detecting analytes, the method comprising, (a) mixing or otherwise contacting a blocked antibody composition with a target sample comprising an analyte wherein a target sequence is coupled to the blocked antibody composition, wherein the blocked antibody composition binds to the analyte, (b) mixing or otherwise contacting an open circle probe (OCP) with the target sample, to produce an OCP-target sample mixture, and incubating the OCP-target sample mixture under conditions that promote hybridization between the open circle probe and the target sequence in the OCP-target sample mixture, (c) mixing or otherwise contacting a ligase with the OCP-target sample mixture, to produce a ligation mixture, and incubating the ligation mixture under conditions that promote ligation of the open circle probe to form an amplification target circle, (d) mixing or otherwise contacting a rolling circle replication primer with the ligation mixture, to produce a primer-ATC mixture, and incubating the primer-ATC mixture under conditions that promote hybridization between the amplification target circle and the rolling circle replication primer in the primer-ATC mixture, and (e) mixing or otherwise contacting DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

As used herein, the term "open circle probe" (or OCP) refers to a single stranded oligonucleotide comprising terminal segments complementary to an oligonucleotide primer sequence. When contacted with a primer, the OCP hybridizes to the primer to form an open circle in which the 5'- and 3'-ends are adjacent. Treatment with a ligase or other chemical entity then joins the 3'- and 5'-nucleotides of the OCP to form a complete circle (i.e., an amplification target circle or ATC) which now provides a template for rolling circle amplification starting from the 3'-end of the primer. Of course, to produce the open circle probe the terminal segments of said probe must be complementary to contiguous segments of the RCA primer sequence. Such probes, primers and methods are well known in the literature (see: Lizardi, U.S. Pat. No. 5,854,033, issued Dec. 29, 1998, the disclosure of which is hereby incorporated by reference in its entirety). In general, any type of rolling circle amplification (RCA) can be used to detect and quantitate the immunoglobulin complexes formed through the process of the invention and are in no way limiting of the invention disclosed herein.

In a preferred embodiment thereof, the present invention further relates to a process for detecting proteins, the method comprising the steps of:

(a) mixing or otherwise contacting a blocked antibody composition with a target sample comprising a target molecule wherein a target sequence is coupled to the blocked antibody composition, wherein the blocked antibody composition binds to the target molecule, wherein the target molecule is a protein, (b) mixing or otherwise contacting an open circle probe with the target sample, to produce an OCP-target sample mixture, and incubating the OCP-target sample mixture under conditions that promote hybridization between the open circle probe and the target sequence in the OCP-target sample mixture, (c) mixing or otherwise contacting a ligase with the OCP-target sample mixture, to produce a ligation mixture, and incubating the ligation mixture under conditions that promote ligation of the open circle probe to form an amplification target circle, (d) mixing or otherwise contacting a rolling circle replication primer with the ligation mixture, to produce a primer-ATC mixture, and incubating the primer-ATC mixture under conditions that promote hybridization between the amplification target circle and the rolling circle replication primer in the primer-ATC mixture, and (e) mixing or otherwise contacting a DNA polymerase with the primer-ATC mixture, to produce a polymerase-ATC mixture, and incubating the polymerase-ATC mixture under conditions that promote replication of the amplification target circle, wherein replication of the amplification target circle results in the formation of tandem sequence DNA.

DNA polymerases useful in the rolling circle replication step of RCA must perform rolling circle replication of primed single-stranded circles (or each strand of a duplex substrate). Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ATC. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., Gene 84:247 (1989)), phage PRD1 DNA polymerase (Jung et al., *Proc. Natl. Acad. Sci. USA* 84:8287 (1987), and Zhu and Ito, *Biochim. Biophys. Acta.* 1219:267–276 (1994)), VENT.RTM. DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), and T4 DNA polymerase holoenzyme (Kaboord and Benkovic, *Curr. Biol.* 5:149–157 (1995)). φ-29 DNA polymerase is most preferred. Equally preferred polymerases include T7 native polymerase, *Bacillus stearothermophilus* (Bst) DNA polymerase, *Thermoanaerobacter thermohydrosulfuricus* (Tts) DNA polymerase (U.S. Pat. No. 5,744,312), and the DNA polymerases of *Thermus aquaticus, Thermus flavus* or *Thermus thermophilus.* Equally preferred are the φ29-type DNA polymerases, which are chosen from the DNA polymerases of phages: φ29, Cp-1, PRD1, φ15, φ21, PZE, PZA, Nf, M2Y, B103, SF5, GA-1, Cp-5, Cp-7, PR4, PR5, PR722, and L17. In a specific embodiment, the DNA polymerase is bacteriophage φ29 DNA polymerase wherein the multiple primers are resistant to exonuclease activity and the target DNA is high molecular weight linear DNA.

For carrying out a ligation step many suitable ligases are known, such as T4 DNA ligase, *E. coli* DNA ligase, Taq DNA ligase, Tth DNA ligase, *Thermus scotoductus* DNA ligase, *Rhodothermus marinus* DNA ligase, Ampligase™, Bst ligase, T4 RNA ligase and cappases.

References for Protein Arrays

1. Mendoza, L. G., McQuary, P., Mongan, A., R. Gangadharan, R., Brignac, S. & Eggers, M. High-throughput microarray-based enzyme-linked immunoabsorbant assay (ELISA). *Biotechniques* 27, 778–788 (1999).
2. Haab, B. B., Dunham, M. J. & Brown P. O. Protein microarrays for highly parallel detection and quantitation of specific proteins and antibodies in complex solutions. *Genome Biology* 2, 1–13 (2001)

3. Schweitzer, B., Wiltshire, S., Lambert, J., O'Malley, S., Kukanskis, K., Zhu, Z., Kingsmore, S. F., Lizardi, P. M. & Ward, D. C. Immunoassays with rolling circle DNA amplification: a versatile platform for ultrasensitive antigen detection. *Proc. Natl. Acad. Sci. (USA)* 97, 10113–10119 (2000).

4. MacBeath, G. &. Schreiber, S. L Printing proteins as microarrays for high-throughput function determination. *Science* 289, 1760–1763 (2000).

What is claimed is:

1. A blocked immunoglobulin comprising an antibody portion and a Protein A portion wherein said antibody portion comprises a member selected from the group consisting of two antibody light chain variable regions, two antibody heavy chain variable regions and a combination thereof.

2. The blocked immunoglobulin of claim 1 wherein said antibody portion comprises at least one antibody light chain variable region.

3. The blocked immunoglobulin of claim 1 wherein said antibody portion comprises at least one antibody heavy chain variable region.

4. The blocked immunoglobulin of claim 1 wherein said antibody portion comprises at least one antibody light chain variable region and at least one antibody heavy chain variable region.

5. The blocked immunoglobulin of claim 1 wherein said antibody portion comprises at least one antigen-reactive fragment.

6. The blocked immunoglobulin of claim 1 wherein said Protein A portion comprises at least one protein A compound.

7. The blocked immunoglobulin of claim 6 wherein said Protein A compound is a fragment of Protein A.

8. The blocked immunoglobulin of claim 1 further comprising a solid support to which said immunoglobulin is attached.

9. The blocked immunoglobulin of claim 8 wherein said immunoglobulin is attached to said solid support through a covalent linkage.

10. The blocked immunoglobulin of claim 8 wherein the antibody portion of said immunoglobulin is attached to said solid support.

11. The blocked immunoglobulin of claim 8 wherein the antibody portion of said immunoglobulin is attached to said solid support through a tether.

12. The blocked immunoglobulin of claim 8 wherein the Protein A portion of said immunoglobulin is attached to said solid support.

13. The blocked immunoglobulin of claim 8 wherein the Protein A portion of said immunoglobulin is attached to said solid support through a tether.

14. The immunoglobulin of claim 8 wherein the solid support is made of a material selected from the group consisting of acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids.

15. The blocked immunoglobulin of claim 8 wherein the solid support further comprises a member selected from the group consisting of thin film, membrane, bottles, dishes, fibers, woven fibers, shaped polymers, particles, beads, microparticles, and a combination of the foregoing.

* * * * *